United States Patent
Shen et al.

(10) Patent No.: US 9,901,356 B2
(45) Date of Patent: Feb. 27, 2018

(54) SYSTEMS AND METHODS FOR MONITORING A SURGICAL PROCEDURE WITH CRITICAL REGIONS

(71) Applicant: THINK SURGICAL, INC., Fremont, CA (US)

(72) Inventors: Feimo Shen, Fremont, CA (US); In K. Mun, Fremont, CA (US); Denise A. Miller, Fremont, CA (US); Bryan Z. Wei, Fremont, CA (US); James P. Morash, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 311 days.

(21) Appl. No.: 14/776,599

(22) PCT Filed: Mar. 14, 2014

(86) PCT No.: PCT/US2014/027627
§ 371 (c)(1),
(2) Date: Sep. 14, 2015

(87) PCT Pub. No.: WO2014/152694
PCT Pub. Date: Sep. 25, 2014

(65) Prior Publication Data
US 2016/0030115 A1 Feb. 4, 2016

Related U.S. Application Data (60) Provisional application No. 61/786,125, filed on Mar. 14, 2013.

(51) Int. Cl.
*A61B 17/17* (2006.01)
*A61B 17/34* (2006.01)
(Continued)

(52) U.S. Cl.
CPC ...... *A61B 17/1703* (2013.01); *A61B 17/3209* (2013.01); *A61B 17/32053* (2013.01);
(Continued)

(58) Field of Classification Search
CPC ... A61B 17/03; A61B 17/32; A61B 17/32053; A61B 17/3209; A61B 17/32093;
(Continued)

(56) References Cited

U.S. PATENT DOCUMENTS

| 4,945,914 A | 8/1990 | Allen |
|---|---|---|
| 4,991,579 A | 2/1991 | Allen |

(Continued)

FOREIGN PATENT DOCUMENTS

| KR | 101039108 B1 | 6/2011 |
|---|---|---|
| KR | 1020120126679 A | 11/2012 |
| WO | 9107726 A1 | 5/1991 |

OTHER PUBLICATIONS

Ault, Thomas et al. "Frameless Patient Registration Using Ultrasonic Imaging", The Robotics Institute, School of Computer Science, Carnegie Mellon University, Pittsburgh, PA, May 14, 1995, pp. 1-9.

(Continued)

*Primary Examiner* — Ryan J Severson
(74) *Attorney, Agent, or Firm* — Avery N. Goldstein; Blue Filament Law, PLLC (57) ABSTRACT

Systems and methods for monitoring an operative site during a surgical procedure using a computer controlled surgical device. In general the methods include the steps of processing one or more defined cutting paths having one or more cut regions; determining a correlation between the cut region and one or more critical regions to generate an alert, wherein the alert indicates a movable end-effector is within a defined proximity of the critical region; and requiring a (Continued)

user acknowledgment of the alert to allow processing of the cutting path to continue. Also described herein are systems and methods for minimizing user fatigue during a semi-computer controlled surgical procedure. In general the methods includes the step of requiring a user generated acknowledgment in response to a computer generated alert, wherein the user acknowledgment is generated using a user controller, the user controller being minimally intrusive to the user experience.

23 Claims, 6 Drawing Sheets

(51) Int. Cl.
| | |
|---|---|
| B25J 9/16 | (2006.01) |
| A61B 17/3205 | (2006.01) |
| A61B 17/3209 | (2006.01) |
| A61B 34/30 | (2016.01) |
| A61B 17/00 | (2006.01) |
| A61B 17/16 | (2006.01) |
| A61B 17/32 | (2006.01) |
| A61B 34/10 | (2016.01) |
| A61B 90/00 | (2016.01) |
| A61B 34/20 | (2016.01) |

(52) U.S. Cl.
CPC .......... *A61B 17/3403* (2013.01); *A61B 34/30* (2016.02); *B25J 9/1676* (2013.01); *A61B 90/03* (2016.02); *A61B 2017/00119* (2013.01); *A61B 2017/00123* (2013.01); *A61B 2017/00367* (2013.01); *A61B 2017/00973* (2013.01); *A61B 2017/1602* (2013.01); *A61B 2017/320052* (2013.01); *A61B 2034/104* (2016.02); *A61B 2034/105* (2016.02); *A61B 2034/107* (2016.02); *A61B 2034/2065* (2016.02); *A61B 2090/08021* (2016.02); *A61B 2090/3762* (2016.02); *A61B 2560/0223* (2013.01); *A61B 2560/0475* (2013.01); *A61B 2576/00* (2013.01); *G05B 2219/45168* (2013.01)

(58) Field of Classification Search
CPC . A61B 17/34; A61B 17/3401; A61B 17/3403; A61B 2017/00115; A61B 2017/00119; A61B 2017/00123; A61B 2017/320052; A61B 2017/3405; A61B 2017/3407; A61B 2017/3409; A61B 2017/3413; A61B 2034/101; A61B 2034/102; A61B 2034/104; A61B 2034/105; A61B 2034/107; A61B 2034/108; A61B 2034/304; A61B 2090/0801; A61B 2090/08021; A61B 2090/0807; A61B 2090/364; A61B 2090/367; A61B 34/00; A61B 34/10; A61B 34/25; A61B 34/30; A61B 34/32; A61B 34/35; A61B 34/37; A61B 34/75; A61B 90/37; B25J 9/1676
See application file for complete search history.

(56) References Cited

U.S. PATENT DOCUMENTS

| | | | |
|---|---|---|---|
| 5,086,401 A | 2/1992 | Glassman et al. | |
| 5,094,241 A | 3/1992 | Allen | |
| 5,097,839 A | 3/1992 | Allen | |
| 5,119,817 A | 6/1992 | Allen | |
| 5,142,930 A | 9/1992 | Allen et al. | |
| 5,198,877 A | 3/1993 | Schulz | |
| 5,211,164 A | 5/1993 | Allen | |
| 5,222,499 A | 6/1993 | Allen et al. | |
| 5,230,338 A | 7/1993 | Allen et al. | |
| 5,383,454 A | 1/1995 | Bucholz | |
| 5,397,329 A | 3/1995 | Allen | |
| 5,769,092 A | 6/1998 | Williamson, Jr. | |
| 5,776,136 A | 7/1998 | Sahay et al. | |
| 5,806,518 A | 9/1998 | Mittelstadt | |
| 5,824,085 A | 10/1998 | Sahay et al. | |
| 5,951,475 A | 9/1999 | Gueziec et al. | |
| 6,033,415 A | 3/2000 | Mittelstadt et al. | |
| 6,119,033 A | 9/2000 | Spigelman et al. | |
| 6,275,233 B1 | 8/2001 | Gueziec | |
| 6,322,567 B1 | 11/2001 | Mittelstadt et al. | |
| 8,315,689 B2* | 11/2012 | Jenkins | G01R 33/286 600/410 |
| 8,615,286 B2* | 12/2013 | Shen | A61B 34/20 600/424 |
| 8,709,016 B2* | 4/2014 | Park | A61B 90/13 606/91 |
| 8,812,077 B2* | 8/2014 | Dempsey | A61N 5/1045 600/410 |
| 9,259,290 B2* | 2/2016 | Jenkins | A61B 5/415 |
| 9,585,725 B2* | 3/2017 | Bonutti | A61B 17/0401 |
| 9,629,687 B2* | 4/2017 | Bonutti | A61B 34/30 |
| 2009/0171184 A1* | 7/2009 | Jenkins | G01R 33/286 600/411 |
| 2010/0312095 A1 | 12/2010 | Jenkins et al. | |
| 2011/0112397 A1* | 5/2011 | Shen | A61B 34/20 600/424 |
| 2011/0152871 A1 | 6/2011 | Park et al. | |
| 2012/0165652 A1 | 6/2012 | Dempsey | |
| 2016/0030115 A1* | 2/2016 | Shen | B25J 9/1676 606/130 |
| 2016/0038243 A1* | 2/2016 | Miller | A61B 17/17 606/130 |

OTHER PUBLICATIONS

Cain, P. et al. "Safety Considerations in a Surgical Robot", Integrated Surgical Systems, Inc., Sacramento, CA, © ISA, 1993—Paper #93-035, pp. 291-294.

Grimson, E. et al. "Automated Registration for Enhanced Reality Visualization in Surgery", AAAI Technical Report SS-94-05. Compilation copyright © 1994, AAAI (www.aaai.org), pp. 26-29.

Kazanzides, P. et al. "Architecture of a Surgical Robot", Integrated Surgical Systems, Inc., 829 W. Stadium Lane, Sacramento, CA, © 1992 IEEE, pp. 1624-1629.

Kazanzides, P. et al. "Force Sensing and Control for a Surgical Robot" Integrated Surgical Systems, 829 West Stadium Lane, Sacramento, CA, and IBM T.J. Watson Research Center, P.O. Box 704, Yorktown Heights, NY, Proceedings of the 1992 IEEE, International Conference on Robotics and Automation, Nice, France, May 1992, pp. 612-617.

Kazanzides, P. et al. "Surgical and Industrial Robots: A Comparison and Case Study", Integrated Surgical Systems, Inc., 829 W. Stadium Lane, Sacramento, CA, 1993 International Robots and Vision Automation Conference, Detroit, Michigan, pp. 1-9.

Lavallée, S., Ph.D., et al. "Computer-Assisted Spine Surgery: A Technique for Accurate Transpedicular Screw Fixation Using CT Data and a 3-D Optical Localizer, Faculte de Medécine de Grenoble, TIMC-IMAG (S.L., P.S., J.T., P.C.), La Tronche, France; Services de Chirurgie Orthopedique, CHU (P.M.), Grenoble, La Tranche, France, Journal of Image Guided Surgery, 1995, pp. 65-73.

Lea, Jon T. et al. "Registration and Immobilization in Robot-Assisted Surgery" Department of Mechanical Engineering, Northwestern University, Evanston, IL and Department of Orthopedic Surgery, Northwestern University Medical School, Chicago, IL, Proceedings of the First International Symposium on Medical Robotics and Computer Assisted Surgery, Pittsburgh, PA, Sep. 1994, pp. 1-11.

Mittelstadt, Brent et al. "Development of a Surgical Robot for Cementless Total Hip Replacement", Integrated Surgical Systems, Inc., 829 West Stadium Lane, Sacramento, CA, Robotica, vol. 11, (56) References Cited

OTHER PUBLICATIONS

Issue 6, Nov. 1993, pp. 553-560,Cambridge University Press, http://journals.cambridge.org/ROB.

Mittelstadt, Brent et al. "Robotic Surgery: Achieving Predictable Results in an Unpredictable Environment", Integrated Surgical Systems, Inc., 829 W. Stadium Lane, Sacramento, CA, '93 ICAR, pp. 367-372.

Paul, Howard A. et al. "Development of a Surgical Robot for Cementless Total Hip Arthroplasty", Integrated Surgical Systems, 829 W. Stadium Lane, Sacramento, CA, Clinical Orthopaedics and Related Research, Apr. 21, 1992, pp. 57-66.

Simon, David A. et al. "Techniques for Fast and Accurate Intra-Surgical Registration", Robotics Institute, Carnegie Mellon University, Pittsburgh, PA, The Journal of Image Guided Surgery, vol. 1, No. 1., Apr. 1995, pp. 1-19.

\* cited by examiner

SYSTEMS AND METHODS FOR MONITORING A SURGICAL PROCEDURE WITH CRITICAL REGIONS

CROSS-REFERENCE TO RELATED APPLICATION

This application claims priority of U.S. Provisional Patent Application Ser. No. 61/786,125 filed Mar. 14, 2013, which is incorporated herein by reference.

INCORPORATION BY REFERENCE

All publications and patent applications mentioned in this specification are herein incorporated by reference in their entirety, as if each individual publication or patent application was specifically and individually indicated to be incorporated by reference in its entirety.

FIELD OF THE INVENTION

This invention relates generally to robotics, medical imaging techniques and procedures, and more particularly to methods for monitoring a robotically assisted surgery involving defined anatomically critical regions.

BACKGROUND OF THE INVENTION

Robotic systems for assisting in a number of medical procedures have been proposed and implemented including neurosurgical, laparoscopic, and orthopedic procedures.

Computers are increasingly used to plan such complex surgeries by analyzing preoperative medical images such as Computed Tomography (CT) or Magnetic Resonance Imaging (MRI) scans of a patient. In order to execute the surgical plan, it is important to accurately align or register the three-dimensional (3D) preoperative data to an actual location of the anatomical features of interest during surgery. Further, when performing robotically assisted surgery, (for example, total hip replacement—when cutting a cavity into a patient's femur bone for the insertion of an artificial hip joint therein), it is very important to ensure anatomically critical regions are monitored with sufficient attention.

There may be a hazard when a medical device operates on a human with indirect surgeon's control. For example, during computer-controlled surgical operations with active surgical devices, the surgeon's monitoring of the operative site is required to ensure safety and efficacy. There may further be a hazard when the operator (synonymously a user or surgeon) is not aware of undesirable cutting performed by the surgical device if the area of cutting is obscured from the user or the user's attention is diverted. This hazard can potentially cause harm to the patient if a warning is not present and corrections are not made.

It is also important to consider the operator's freedom of movement during the procedure. For example, an operator that is required to actively engage with the medical device as it is operating can easily become fatigued.

Accordingly, in order to mitigate this hazard it has been desirable to attempt to determine anatomically critical regions that should be monitored during a computer-controlled surgical procedure and alert the operator during the surgery in situ. An operator controller can be added to the surgical device as a vigilance control which requires the surgeon to acknowledge the alert for active cutting to continue.

The ORTHODOC presurgical planning workstation and the ROBODOC robotic surgical system are described in a number of references, including the following: (1) Kazanzides, P., Zuhars, J., Mittelstadt, B. D., Taylor, R. H.: "Force Sensing and Control for a Surgical Robot," Proc. IEEE Conference. on Robotics & Automation, Pages 612-616, Nice, France, May 1992. (2) Kazanzides, P., Zuhars, J., Mittelstadt, B. D., Williamson, B., Cain, P., Smith, F., Rose, L., Mustis, B.: "Architecture of a Surgical Robot," Proc. IEEE Conference. on Systems, Man, and Cybernetics, Chicago, Ill., Pages 1624-1629, October, 1992. (3) Paul, H. A., Bargar, W. L., Mittelstadt, B., Musits, B., Taylor, R. H., Kazanzides, P., Zuhars, J., Williamson, B., Hanson, W.: "Development of a Surgical Robot For Cementless Total Hip Arthroplasty," Clinical Orthopaedics, Volume 285, Pages 57-66, December 1992. (4) Kazanzides, P., Mittelstadt, B. D., Zuhars, J., Cain, P., Paul, H. A., "Surgical and Industrial Robots: Comparison and Case Study," Proc. International Robots and Vision Automation Conference, Pages 1019-1026, Detroit, Mich., April 1993. (5) Mittelstadt, B., Kazanzides, P., Zuhars, J., Williamson, B., Pettit, R., Cain, P., Kloth, D., Rose, L., Musits, B.: "Development of a surgical robot for cementless total hip replacement," Robotica, Volume 11, Pages 553-560, 1993. (6) Mittelstadt B., Kazanzides, P., Zuhars, J., Cain, P., Williamson, B.: "Robotic surgery: Achieving predictable results in an unpredictable environment," Proc. Sixth International Conference on Advanced Robotics, Pages 367-372, Tokyo, November, 1993. (7) Cain, P., Kazanzides, P., Zuhars, J., Mittelstadt, B., Paul, H.: "Safety Considerations in a Surgical Robot," Biomedical Sciences Instrumentation, Volume 29, Pages 291-294, San Antonio, Tex., April 1993. (8) Mittelstadt, B. D., Kazanzides, P., Zuhars, J., Williamson, B., Cain, P., Smith, F. Bargar, W.: "The Evolution of A Surgical Robot From Prototype to Human Clinical Use," in Proc. First International Symposium on Medical Robotics and Computer Assisted Surgery, Volume I, Pages 36-41, Pittsburgh, Pa., September 1994.

Other publications which describe image registration in robotic surgical and other procedures include the following: (9) Grimson, W. E. L., Lozano-Perez, T., Wells III, W. M., Ettinger, G. J., White, S. J., Kikinis, R.: "Automated Registration for Enhanced Reality Visualization in Surgery," Proceedings of the First International Symposium on Medical Robotics and Computer Assisted Surgery, Volume I, Sessions I-III, Pages 82-89, Pittsburgh, Pa., Sep. 22-24, 1995. (10) Nolte, L. P., Zamorano, L. J., Jiang, Z., Wang, Q., Langlotz, F., Arm, E., Visarius, H.: "A Novel Approach to Computer Assisted Spine Surgery," Proceedings of the First International Symposium on Medical Robotics and Computer Assisted Surgery, Volume II, Session IV, Pages 323-328, Pittsburgh, Pa., Sep. 22-24, 1994. (11) Lavallee, S., Sautot, P., Troccaz, J., Cinquin, P., Merloz, P.: "Computer Assisted Spine Surgery: a technique for accurate transpedicular screw fixation using CT data and a 3-D optical localizer," Proceedings of the First International Symposium on Medical Robotics and Computer Assisted Surgery, Volume II, Session IV, Pages 315-321, Pittsburgh, Pa., Sep. 22-24, 1994. (12) Potamianos, P., Davies, B. L., Hibberd, R. D.: "Intra-Operative Imaging Guidance For Keyhole Surgery Methodology and Calibration," Proceedings of the First International Symposium on Medical Robotics and Computer Assisted Surgery, Volume I, Sessions I-III, Pages 98-104, Pittsburgh, Pa., Sep. 22-24, 1994. (13) Simon, D. A., Hebert, M., Kanade, T.: "Techniques for Fast and Accurate Intra-Surgical Registration," Proceedings of the First International Symposium on Medical Robotics and Computer Assisted Surgery, Volume I, Sessions I-III, Pages 90-97, Pittsburgh, Pa., Sep. 22-24, 1995. (14) Peria, O., Francois-Joubert, A., Lavallee, S., Champleboux, G., Cinquin, P., Grand, S.: "Accurate Registration of SPECT and MR brain images of patients suffering from epilepsy or tumor," Proceedings of the First International Symposium on Medical Robotics and Computer Assisted Surgery, Volume II, Session IV, Pages 58-62, Pittsburgh, Pa., Sep. 22-24, 1995. (15) Lea, J. T., Watkins, D., Mills, A., Peshkin, M. A., Kienzle III, T. C., Stulberg, D. S.: "Registration and Immobilization for Robot-Assisted Orthopaedic Surgery," Proceedings of the First International Symposium on Medical Robotics and Computer Assisted Surgery, Volume I, Sessions I-III, Pages 63-68, Pittsburgh, Pa., Sep. 22-24, 1995. (16) Ault, T., Siegel, M. W.: "Frameless Patient Registration Using Ultrasonic Imaging," Proceedings of the First International Symposium on Medical Robotics and Computer Assisted Surgery, Volume I, Sessions I-III, Pages 74-81, Pittsburgh, Pa., Sep. 22-24, 1995. (17) Champleboux, G., Lavallee, S., Cinquin, P.: "An Optical Conformer for Radiotherapy Treatment Planning," Proceedings of the First International Symposium on Medical Robotics and Computer Assisted Surgery, Volume I, Sessions I-III, Pages 69-73, Pittsburgh, Pa., Sep. 22-24, 1995.

Various systems for image registration using fiducial implants are also described in U.S. Pat. Nos. 4,991,579; 4,945,914; 5,094,241; 5,119,817; 5,097,839; 5,142,930; 5,211,164; 5,230,338; 5,222,499; and 5,397,329 to Allen.

A system and method for performing robotically assisted surgery is described in U.S. Pat. No. 5,086,401. Computer-assisted imaging and probe tracking systems are described in U.S. Pat. Nos. 5,383,454; 5,198,877; and WO 91/07726. U.S. Pat. No. 5,806,518 describes a method and system for transforming a bone image into a robotic coordinate system by aligning a robotic probe within the medullary canal of the femur. U.S. Pat. No. 6,033,415 describes a method and system for transforming a bone image into a robotic coordinate system based upon registering between the robotic coordinate system and the image data set 1) two positional coordinates axially spaced apart along the bone and 2) a directional vector passing through at least one of the positional coordinates. Unfortunately, the ability to warn an operator of unintended movement of a surgical robot into critical areas of subject tissue has not been addressed adequately in the prior art.

Thus, there is a need for an improved system and method for monitoring a computer-assisted surgical procedure having critical regions during the procedure. There also exists a need to provide an efficient interface for a user receiving an alert of robotic movement into a critical area.

SUMMARY OF THE INVENTION

Systems and methods for monitoring an operative site during a surgical procedure using a computer controlled surgical device. In general the methods include processing a cutting path having one or more cut regions; determining a correlation between the cut region and one or more critical regions to generate an alert indicative of a movable end-effector being within a defined proximity of one or more critical regions; compromising a subject tissue in the cut region with the computer controlled surgical device and exclusive of the one or more critical regions; and requiring a user acknowledgment of the alert to allow processing of the cutting path to continue. Also described herein are systems and methods for minimizing user fatigue during a semi-computer controlled surgical procedure. In general the methods includes requiring a user generated acknowledgment in response to a computer generated alert, wherein the user acknowledgment is generated using a user controller, the user controller being minimally intrusive to the user experience.

DETAILED DESCRIPTION OF THE INVENTION

The following description of the various embodiments of the invention is not intended to limit the invention to these preferred embodiments, but rather to enable any person skilled in the art to make and use this invention. Disclosed herein are methods for monitoring an operative site of a computer-controlled surgical procedure and methods for preventing user fatigue during a computer-controlled surgical procedure. Also described herein are systems and devices for computer controlled surgical procedures and user controller devices for implementing the methods disclosed herein and minimizing user fatigue. The present invention has utility in robot assisted surgery and systems for performing such surgery.

In general, the methods may include determining a correlation between a cut region (of a cutting path) and one or more critical regions in order to generate an alert that requires a user acknowledgement.

One aspect of the invention includes identifying the critical regions and then processing those critical regions to trigger the alert to the surgeon. The critical regions may be processed in parallel with processing the cutting path (actual cutting). In other words, while (or before) an instruction to cut is sent to the robot, the computer can check for a correlation between the cut region and the identified critical regions which can then trigger the alert.

One inventive concept described herein is a method of mitigating a hazard by alerting the surgeon when the end-effector enters anatomically critical regions (e.g., where critical tissue, vascular, or nerve damage can potentially take place) so appropriate action can be taken to allow cutting to continue or re-arrange the surgery progress. Accordingly, this invention allows surgeon's direct control of an active surgical device during the cutting operation. A 3D image analysis can be performed to determine the critical regions by employing semi-automatic segmentation of imaging data to distinguish critical regions from non-critical regions. The identified critical region information can be stored and then used in parallel with the existing cutting paths taken by the computer-controlled surgical device. As the cutting path is about to enter a critical region at the device operating end-effector, the device displays on a monitor (with or without audio output) to warn the surgeon that the device operating end-effector will be in proximity to important structures inside the critical region. When the critical region is entered, the device can halt cutting. It is appreciated that the scan resolution of a cutting path for surgery may not detect fine structures of capillaries or nerves, that a surgeon may wish to avoid before compromising surgical subject tissue in the course of a surgical procedure. Such areas upon visualization by a user, can be avoided and in some inventive embodiments designated as critical regions for subsequent cut paths.

When the alert is presented to the surgeon, the surgeon is required to acknowledge the alert to allow the device to proceed with cutting. This acknowledgement may be received as a vigilance control button on a pendant that is held by the surgeon. If the acknowledgement is not received, the device will not continue cutting, minimizing the hazard of undesirable cutting that could cause patient harm. However, if the warning is acknowledged before a critical region is entered, there is no interruption to the cutting during the non-critical-to-critical region transition.

In addition, the existing ROBODOC control pendant is not ergonomically designed to depress buttons for long periods. In addition, the buttons use custom built switch mechanisms that may not be configured for optimal operational cycle life.

The systems and methods described herein mitigate the hazard of patient injury by a computer-controlled active surgical device.

Figure 1:
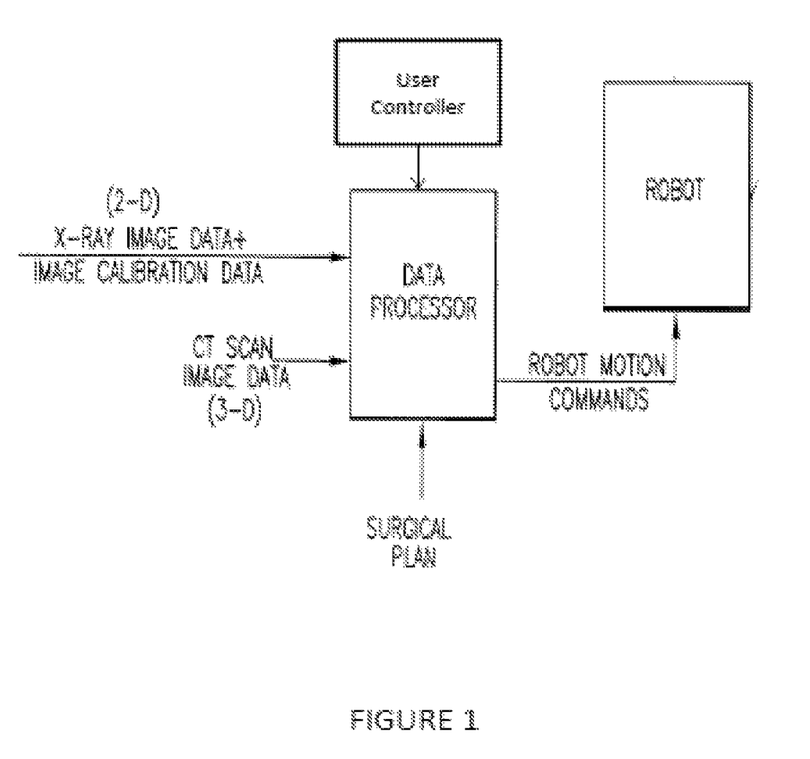
FIG. 1 illustrates a block diagram of a method for monitoring a surgical procedure having critical regions in accordance with some embodiments.

As shown in FIG. 1, 2-D X-ray image data (including calibration data in some embodiments) is input into a data processor 12, which also receives CT or MRI scan data and a surgical plan. The data processor 12 operates on this data, in accordance with the methods described below, so as to output robot motion commands to the robot system 20. In response, the robot performs or assists in the performance of a surgical technique, such as accurately positioning an effector (e.g., a cutting tool) to remove a portion of the bone to receive an implanted device.

Surgical Robotic System

Figure 2:
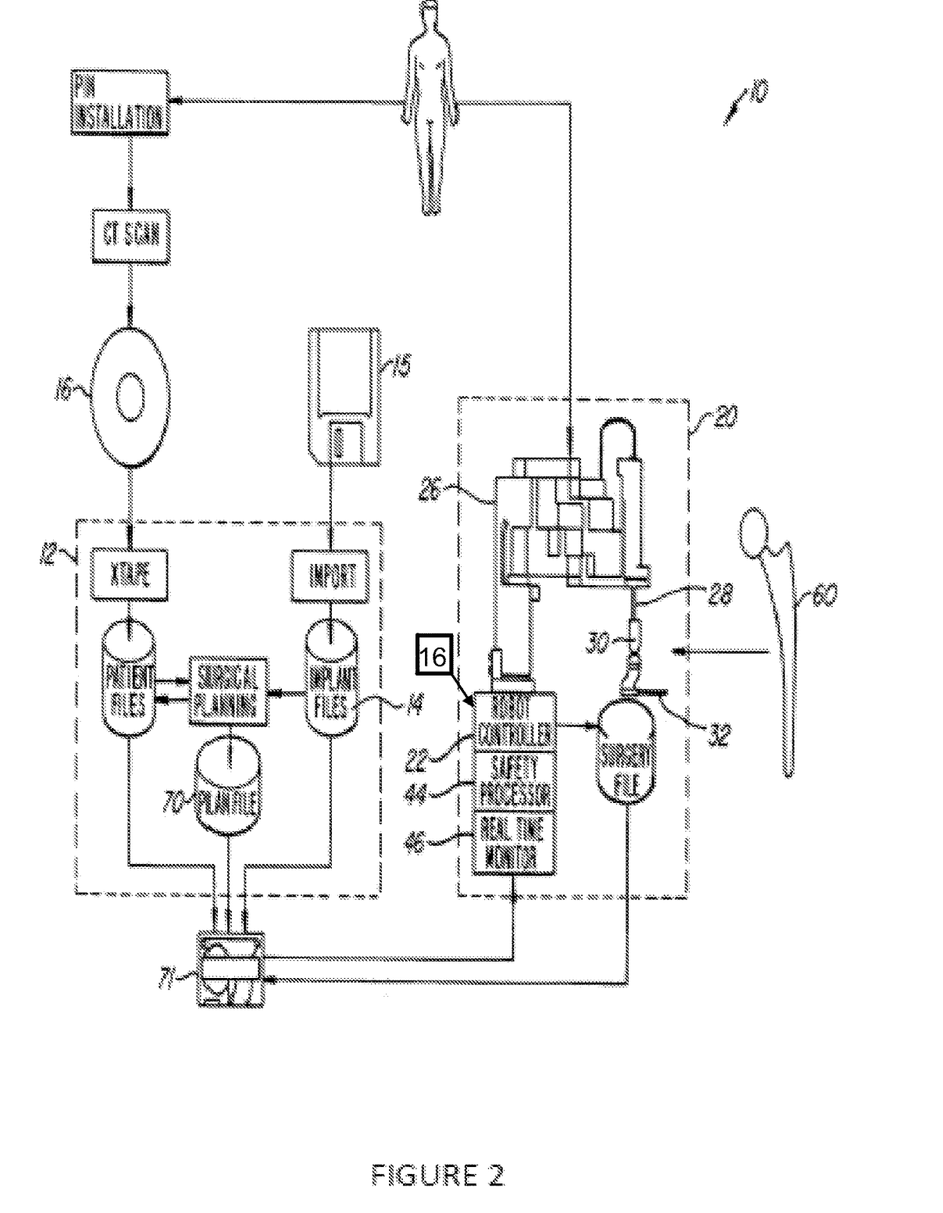
FIG. 2 illustrates the architecture of the surgical robotic system in accordance with an inventive embodiment.

As described, for example, in commonly owned U.S. Pat. Nos. 6,033,415; 5,824,085; 5,806,518; 5,776,136; and 5,769,092, an exemplary system 10 capable of implementing the methods of the present invention for robotic assisted surgery is illustrated in FIG. 2. The system 10 includes both a presurgical planning workstation 12 and a library of implant designs 14, for example, in the form of CAD model data sets 15. A bone image data set 16, for example representative of a CT bone image, is obtained and transferred into the presurgical planning workstation 12. The user, such as a treating physician or an assistant working with the treating physician, is able to work at the presurgical planning workstation to select and position a suitable implant design within the patient's bone. Details of such presurgical planning are well described in the literature relating to the ORTHODOC presurgical planning system cited above.

The system 10 of the present invention includes a robotic operative system 20 which includes a robotic controller 22 (for example, a digital processor in the form of a programmable computer), an online display screen 24, and a robot arm 26. The robot arm can be any conventional industrial robot having a manipulatable surgical robotic arm 28 and in some embodiments having at least 5 axes and capable of high precision placement. In some embodiments, a force sensor 30 is mounted at the distal end of arm 28, and an effector in the form of a probe 32 or a surgical cutting tool (not illustrated) may be attached to the force sensor.

The robotic system 20 further includes a safety processor 44, and a real time monitoring computer 46, as illustrated in FIG. 2. The force sensor 30, the safety processor 44, the real time monitor 46, and a bone motion detector 51 (see FIG. 3), each help monitor the position, slippage, and blockage of the effector end of the manipulatable arm 28. In some embodiments, the bone 60 (e.g. a femur) is held in place in a fixator assembly 52. Real time monitoring of these parameters can help assure that the robotic system is operating as planned. Details of these monitoring systems are described in the literature cited above which describes the ROBODOC robotic surgical system.

In some embodiments, a digitized bone data set includes the coordinate positions of a number of surface locations on the bone as measured by a bone digitizer arm registered to the robotic coordinate system. Accordingly, system 10 further includes bone digitizer arm 100, for example, as described in commonly owned U.S. Pat. No. 6,033,415. An acquired digitized bone data set 16, (shown in FIG. 2 as an input to robotic controller 22), is obtained by a digitizer arm and is used to transform bone image data set 16 into the robotic coordinate system.

Figure 3:
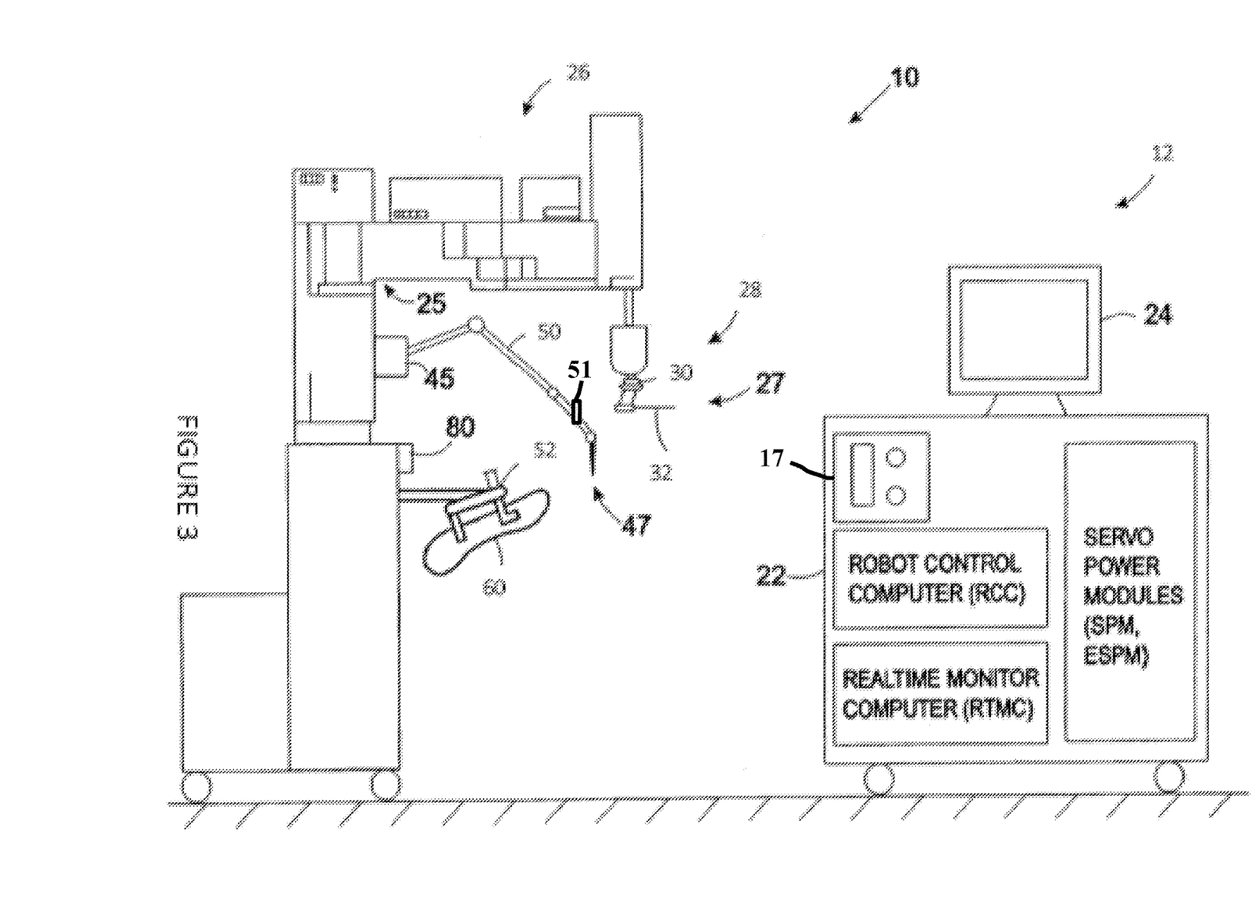
FIG. 3 illustrates the surgical components of the surgical system of FIG. 2.

As seen in FIG. 3 the system 10 includes a passive mechanical arm bone motion detector 51 and a bone fixator 52. The preplanning workstation (user interface) 12 includes a computer 17 and a terminal display 24.

Cutting tool 32 on surgical robotic arm 28 is adapted to cut an implant cavity into the end of bone 60. Fixator 52 is adapted to hold bone 60 in a substantially fixed position during surgery. Each of surgical robotic arm 28, passive mechanical arm 50 and fixator 52 are attached at their proximal ends to robot 26 which acts as a fixed base, preventing any relative motion between proximal ends 25 and 45 of surgical robotic arm 28 and passive mechanical arm 50, respectively.

Connection of both proximal end 45 of passive mechanical arm 50 and proximal end 25 of surgical robotic arm 28 to robot 26 avoids relative motion between ends 25 and 45, such that surgical robotic arm 28 and passive mechanical arm 50 move in the same relative coordinate system.

The system includes various modules as discussed herein. As can be appreciated by one of ordinary skill in the art, each of the modules includes various sub-routines, procedures, definitional statements and macros. Each of the modules are typically separately compiled and linked into a single executable program. Therefore, the description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

As used herein, "instructions" or "command" refer to computer-implemented steps for processing information in the system. Instructions can be implemented in software, firmware or hardware and include any type of programmed step undertaken by components of the system.

A "microprocessor" or "processor" may be any conventional general purpose single- or multi-core microprocessor. In addition, the microprocessor may be any conventional special purpose microprocessor such as a digital signal processor or a graphics processor.

In one example, the system may use separate sub-processes to perform the processes described herein.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

The invention disclosed herein may be implemented as a method, apparatus or article of manufacture using standard programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

In addition, the modules or instructions may be stored onto one or more programmable storage devices, such as FLASH drives, CD-ROMs, hard disks, and DVDs.

Exemplary Devices and Methods for Monitoring a Surgical Procedure

Figure 4:
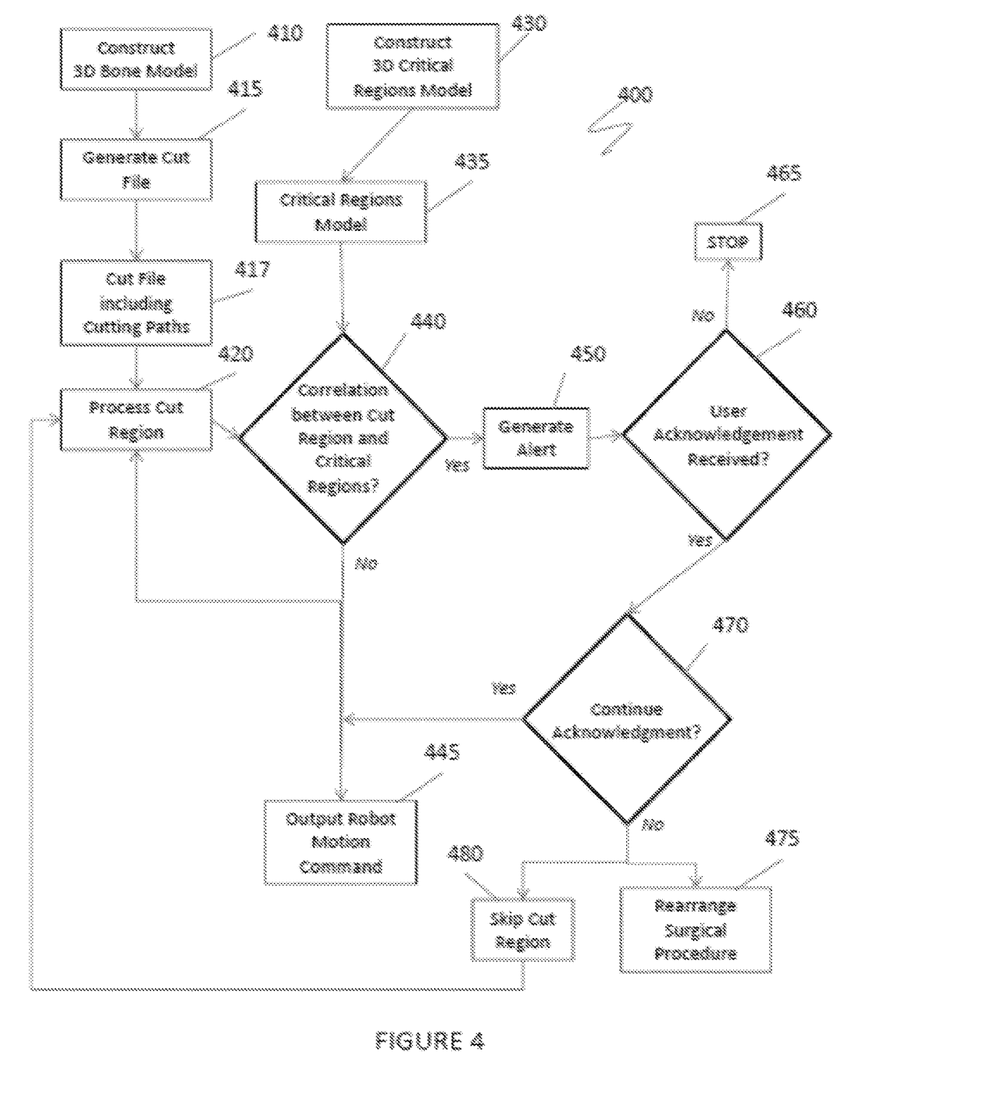
FIG. 4 illustrates a flowchart of a method for monitoring a surgical procedure having critical regions in accordance with some embodiments.

FIG. 4 shows a flowchart illustrating an exemplary process 400 that may run within one implementation of a system 10. Process 400 may be implemented instructions included in the memory, illustrated as part of system 10 in FIG. 2.

As shown in FIG. 4, a method for monitoring a surgical procedure with critical regions of a preferred embodiment may include the steps of processing a cut region in block 420 from a cut path in a cutting file in block 417, determining a correlation between the cut region and the critical regions (block 435) in decision block 440, generating an output robot motion command in block 445, generating an alert in block 450, requesting a user acknowledgment in decision block 460, a default stop command in block 465, determining a value of a user acknowledgment in decision block 470, generating a skip cut region command in block 480, and generating a rearrange surgical procedure command in block 475. In some embodiments, the method further includes at least one of constructing a 3-D bone model in block 410, generating a cut file in block 415, and constructing a 3-D critical regions model in block 430. Each step is described in more detail below.

In some embodiments, process 400 begins at block 435 where a critical region model is received. After receiving a cut file at block 417 the process then moves to block 420 where the system begins processing a cut region of a cutting path in the cut file. As discussed in more detail herein, the cutting path may be processed one cut region at a time or in real-time. The cut file and/or the critical region model can be stored and/or processed in the robotic operative system 20. Alternatively, the cut file and/or the critical region model can be stored and/or processed in the planning workstation 12.

After processing of the cutting path has been initialized and a first cut region has been processed, the process 400 moves to decision block 440, where process 400 evaluates whether a selected correlation between the first cut region and critical regions exists. If it is determined that the selected correlation does not exist, then the process moves to block 420 where processing of the cutting path continues, for example by processing the next cut region in the cutting path. In addition, if it is determined that the selected correlation does not exist, the process moves to block 445 where an output robot motion command is generated for the first cut region.

However, if it has been determined that the selected correlation does exist, the process 400 can continue to block 450 where an alert command is generated. As discussed in more detail herein, the alert command can include at least one of a visual or audio output command. The alert command can be stored and/or processed in the robotic operative system 20. Alternatively, the alert command can be stored and/or processed in the planning workstation 12. Further yet, the alert command can be stored and/or processed in a user controller, such as a pendant. A suitable user controller is discussed in more detail below. The alert command can be used to generate an alert (visual and/or auditory) for example in the online display screen 24 and/or on the user controller.

The process 400 then requires a user acknowledgment to continue processing the cutting path. A determination is made at decision block 460 whether or not an acknowledgment has been received. If it is determined that no user acknowledgment has been received, the process moves to block 465 where a stop command is generated. In some embodiments, the process 400 will not resume until a user acknowledgment is received, for example the process can have a default stop command. However, if a user acknowledgment is received, the process 400 moves to decision block 470. A determination is made at decision block 470 what type or value of acknowledgment has been received. The type or value of the acknowledgment can include, but is not limited to "continue", "skip cut region", "rearrange surgical procedure", "slow cut rate", "pause", "stop", or the like. If a "skip cut region" command is received, for example, the process 400 will continue to block 420 where the process 400 continues to process the cutting path (for example, by processing the next cut region in the cutting path) without generating an output robot motion command for the instant cut region. However, if a "continue" command is received, the process 400 continues to process the cutting path and generates an output robot motion command for the instant cut region.

A user acknowledgment command can be received from one or more sources. For example, a user acknowledgment command can be received from the user controller as described in more detail below. Alternatively, or in addition, a user acknowledgment can be received from any suitable user input point in the system 10, such as robotic operative system 20 and/or the robotic controller 22.

Output robot motion commands or instructions block 450 can be stored in the system, for example, in a memory of the planning workstation 12, and later accessed by the robotic operative system 20. Alternatively, the output robot motion commands or instructions can be stored in a memory of the robotic operative system 20.

Process 400 can continue to run (iteratively) until each of the cut regions in the cut file have been processed or until a "stop" command is received.

Constructing a 3-D Bone Model and Generating a Cut File

As shown in FIG. 4, process 400 may include a process or routine for generating the cut file at block 415, as discussed in more detail below. In some embodiments, the cut file may be generated using a 3-D bone model, thus process 400 may also include a process or routine for constructing a 3-D bone model at block 410. One approach to constructing a 3D bone model is described in commonly owned U.S. Pat. No. 5,951,475. Example systems and methods are described for accomplishing an anatomy-based registration of three-dimensional data (model data) obtained from a scan, such as a CT scan or an MRI scan, to two dimensional projection data, such as x-ray data, enabling the registration of a surgical robot to a preoperative treatment plan. Also disclosed is a semiautomatic method for registering preoperative CT scan data to a robot used intraoperatively for, by example, Total Hip Replacement Surgery (THR).

Figure 5:
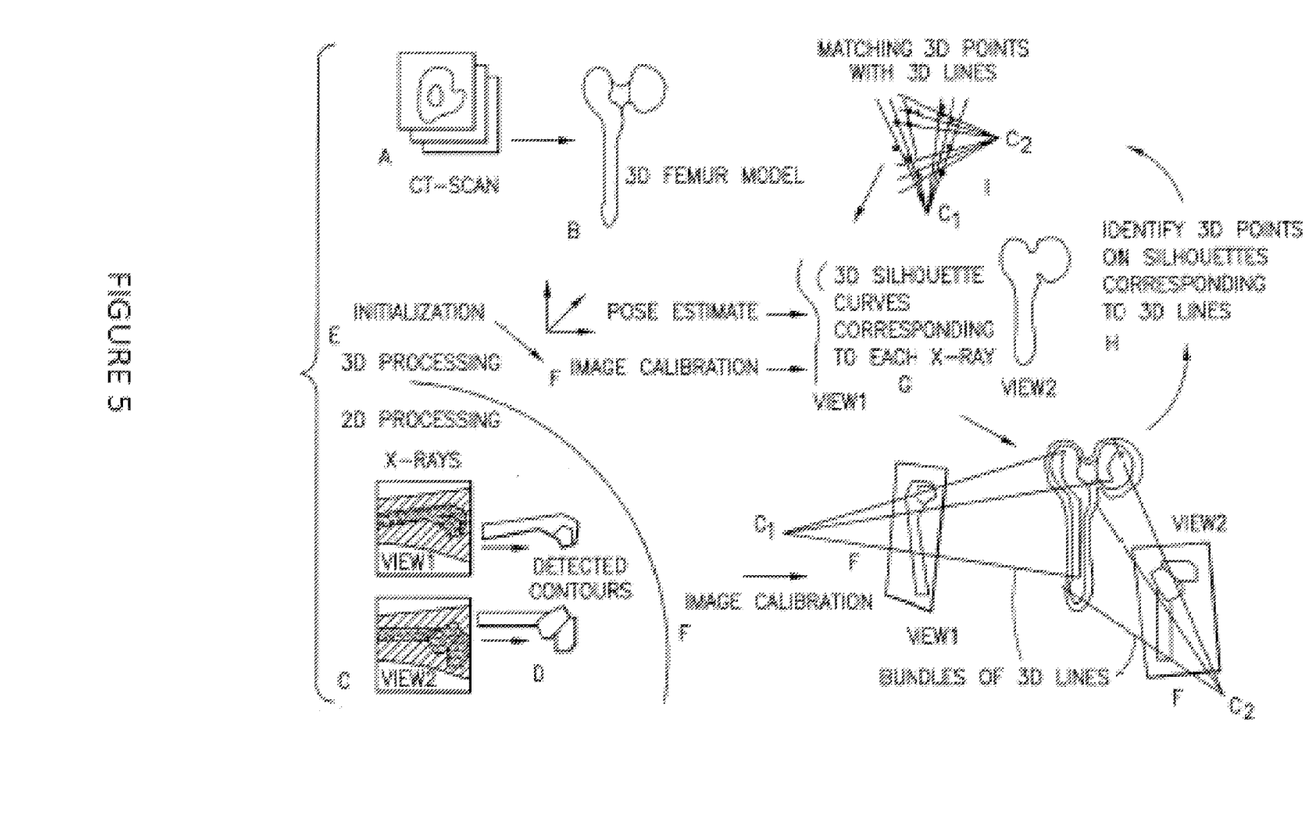
FIG. 5 is a chart illustrating a method for the registration of three dimensional image or surface data to projection data using methods in accordance with some embodiments.

As shown in FIG. 5, at Step A, CT-scan data is obtained, and the resulting image slices are processed at Step B, to yield an accurate 3-D model of the femur (or any other tissue of surgical interest). At Step C, a plurality of x-ray views (e.g., View 1, View 2) of the femur are obtained, the views including the image location calibration markers from the calibration device 12 or 12', and at Step D the x-ray views obtained at Step C are processed to detect contours. At Step E processing is initialized by the data processor 16. At Step F, images are calibrated using the process described above for producing a bundle of 3-D lines passing through the 2-D contours. At Step G pose estimation and image calibration data are used to determine on the 3-D model various 3-D silhouette curves corresponding to each x-ray view. At Step H, the method identifies 3-D points on the silhouette curves that correspond to 3-D lines, and at Step I, a matching process is performed to match 3-D points with 3-D lines. The Steps G, H and I are iterated one or more times until the femur surface model data and the x-ray image data converges, resulting in a calibration of the x-ray data to the femur model.

Segmentation of Bony Anatomy from Computed Tomography Data

A surface model can be extracted from the CT-scan using a semiautomatic method. In a test CT scan, the slice spacing was found to vary widely, from 1 to 3 to 6 and finally to 120 mm. Such a variation can be expected in practice so as to maximize the detail in the critical areas while limiting the x-ray dosage. As such, iso-surface algorithms for surface extraction can be effectively ruled out, since they suffer from poor contour definition at the slice level and poor surface tiling between contours.

Instead, the following algorithm is preferred: for each slice, use an active contour model to detect the contour of the bone, as was previously done for radiographs. Contours are approximated to within 0.1 to 0.3 millimeters and are tiled together in an optimal fashion, such that the average triangle compactness is maximized. Triangle compactness is defined herein as a ratio: (4*sqrt 3*area of the triangle) divided by the sum of the squares of the lengths of the sides of the triangle. The optimum triangulation can be obtained using dynamic programming, and is thus computationally affordable. The resulting surface is an oriented manifold with, typically, two boundaries. The contours forming the surface as well as their level of detail are gathered in a script file that completely determines the surface. The script file can be easily edited for examining various levels of details, or adding or omitting particular slices.

The resulting surface is then approximated with a tolerance of 0.3 mm using, in a preferred embodiment, a method described by Andre P. Gueziec, "Surface simplification with variable tolerance", MRCASII, pages 132-139, Baltimore, Md., November 1995. In the final surface both the proximal and distal regions are incomplete, and that there is a gap of 120 mm between two slices situated distally. The final surface of the model contains 3,460 triangles, which is considered very compact.

A more detailed description of a preferred method for building a 3-D model of the bone from a set of 2D Slices of Computed Tomography (CT) image data is provided in commonly owned U.S. Pat. No. 5,951,475. For purposes of continuity herein, a summary of the method is provided below.

A method for building the model in a specific inventive embodiment entails the following steps. In a first step, active contour software is used to extract the outer contours of the bone for each slice of CT data. Active contours are described in Kass, Witkin and Terzopoulos's "Snakes: Active Contour Models", in proceedings of the First International Conference on Computer Vision, 1987. In this technique, an operator selects a number of control points (CPs) by "pointing and clicking" inside the CT image in the vicinity of the structures of interest. The system then constructs a polygonal curve linking the control points, and then modifies the polygonal curve to minimize an expression combining a measure of curve length, a measure of average curvature of the curve, a measure of an image potential average curvature of the curve, and a measure of an image potential. Generally, the potential equals the squared norm of the image gradient. If $I(x,y)$ is the image intensity of a pixel of location $(x,y)$, the image gradient grad (I) is a vector whose first coordinate is the derivative of I with respect to x, and whose second coordinate is the derivative of I with respect to y. After application of the active contour technique for each slice, one obtains polygonal curve(s) representing the contours(s) of the bone.

In a second step, the method replaces the polygonal curves with approximating polygonal curves containing fewer vertices, such that the approximating polygonal curves do not deviate from the original polygonal curves by more than a pre-specified threshold (e.g., 0.3 millimeters). Each polygonal curve is represented using an ordered array of vertices, and each vertex is indexed with its position in the array. For each polygonal curve, the following process is iterated until the maximum deviation threshold is respected. First compute the maximum deviation between any vertex and the line segment obtained by joining the last vertex with the first vertex. If the maximum deviation computed is larger than the threshold, split the ordered array of vertices into two arrays of equal size (if the number of vertices is even, the first array contains one more vertex than the second array), and then consider the two polygonal curves defined with the resulting array.

In a third step the inventive method builds a surface model made of triangles and that contains every vertex and every edge of the approximating polygonal curves. This third step examines in turn each pair of consecutive slices and builds a surface slab that contains the approximating polygonal curves extracted from both slices.

For the case where there is one curve in the first slice and one curve in the second slice, the method proceeds by using known "dynamic programming" methods described, for example, in Cormen, Leicerson, and Rivest's "Introduction to Algorithms", MIT Press, 1994, to determine a set of triangles. The set of triangles are determined such that each triangle has at least two vertices in different curves, and the sum of triangle compactnesses, as defined above, is minimized among all possible formation of triangles.

In a fourth step the surface slabs built in the third step are combined to form a surface by removing duplicate references to vertices belonging to polygonal curves shared by any two slabs.

In a fifth and last step, the surface resulting from the fourth step is approximated by a surface containing fewer triangles using, for example, the technique described in commonly Assigned U.S. patent application entitled "Surface Simplification Preserving a Solid Volume and Respecting Distance Tolerances", Ser. No. 08/742,641, filed Nov. 1, 1996, by A. Gueziec, and also in the above referenced publication by Andre P. Gueziec, "Surface simplification with variable tolerance", MRCASII, pages 132-139, Baltimore, Md., November 1995. Distance tolerances are specified by an operator. In a typical session, a single global tolerance of 0.2 mm was employed, thus bounding the maximum deviation from the points collected using active contours by 0.2+0.3=0.5 mm.

Although the segmentation method is described with respect to the methods described in U.S. Pat. No. 5,951,475, it is contemplated that segmentation can also be accomplished based on using the radiodensity value of the CT scan data (for example, measured in Hounsfield Units).

Generating a Cut File with Cutting Paths and Cut Regions

As shown in FIG. 4, a specific embodiment for monitoring a surgical procedure with critical regions may include block 415, which recites generating a cut file including cutting paths. Block 415 preferably functions to provide process 400 with a cut file (or preoperative treatment plan) that includes cutting paths having one or more cut regions.

Non-limiting methods of generating cut files of this invention include Primary (PTHR) and Revision (RTHR) Total Hip Replacement Surgery. For example, one suitable approach to generating a cut file for Primary Total Hip Replacement Surgery is described in commonly owned U.S. Pat. No. 5,776,136. Another suitable approach to generating a cut file for example for Revision Total Hip Replacement Surgery is described in commonly owned U.S. Pat. No. 5,769,092.

Constructing a 3D Critical Regions Model

As shown in FIG. 4, process 400 may include a process or routine for constructing the critical regions model at block 415. Block 430 in some embodiments functions to identify critical regions in the operative space.

The term "critical region" is used herein to mean an area of elevated risk which requires a user's attention (and acknowledgment). In some embodiments, a critical region is a region that should not be cut by the robotic system. In some embodiments, a critical region may be cut by the robotic system. In the later embodiments, for example, a critical region includes a buffer zone adjacent to a region that should not be cut by the device. A distance of the buffer zone may be selected at any suitable distance from the region not to be cut.

In some embodiments, the critical region includes cortical bone, which should not be cut, or at least minimally cut. In some embodiments, the critical region includes soft tissues.

Critical regions can be determined based on both known anatomical areas where arteries, veins, nerves bundles, cartilage, ligaments, and tendons are located, and image-based processing to indicate these areas.

In some embodiments, a 3-D analysis is performed to generate a 3-D critical region model. The 3-D analysis can be accomplished by any method suitable for distinguishing critical regions from non-critical regions. In some embodiments, the 3-D analysis is performed with semi-automatic segmentation of imaging data. For example, in some embodiments the semi-automatic segmentation method as used to generate the 3-D bone model described above (with regard to U.S. Pat. No. 5,951,475) can be employed. In some embodiments, the 3-D analysis is performed manually by selection of anatomical regions or any region deemed critical by the user.

Image data used to construct the 3-D critical region model can be acquired from one or more image sources. In some embodiments, the critical region image data is derived from CT scans and/or MRI images. In some embodiments, the critical region image data is derived from CT scans alone. In some embodiments, the source of image data is the same as that used to construct the bone image (likely CT, but possibly MRI). In some embodiments, a combination of CT images can be used to create the bone image and MRI data can be used to locate critical soft tissues (such as ligaments or tendons). In some embodiments, the two image types can be merged into a single model.

The critical regions can be defined based on CT scan data areas that have high density values, such as those representing cortical bone. Additionally, soft tissues attachments can be defined as critical regions using the image data (more likely MRI). Additionally, soft tissues can be defined based on general anatomical models of known ligaments/tendons insertion sites.

A critical region may be defined by any suitable number of pixels. Alternatively, a critical region may be defined by a 3D volume or a single point in space. In some embodiments, the identified critical regions are saved or stored as 3-D volumes.

Although illustrated in FIG. 4 as a block (block 430 and 435) preceding the correlation determination at block 440, the 3-D analysis can be performed at various points in the process 400. For example, the 3-D analysis can be performed before and/or during the surgery (processing the cutting paths). In embodiments where the 3-D analysis is performed during the surgery or after the surgery has begun, the critical regions can be identified after processing of the cutting path has begun and throughout the process.

In some embodiments, it may be advantageous to perform a 3-D analysis and identify critical regions preoperatively (i.e., before the surgery has begun). One example where it might be advantageous is in identifying cortical bone on the images.

In some embodiments, it may be advantageous to perform a 3-D analysis and identify critical regions after the cutting path has begun. One example where it might be advantageous is in identifying soft tissues. For example, in some embodiments, it might be easier to digitize their insertion points after a wound is open. In such embodiments, most of the analysis could take place before cutting has started, but could happen after some cuts have been made, especially as there is more exposure once some cuts have been made. In some embodiments, a first 3-D analysis is performed before the surgery has begun and a second 3-D analysis is performed during the surgery or after the surgery as begun.

The stored critical region data is used in parallel with the existing paths taken by the computer-controlled surgical device. For example, during computer-controlled cutting, the critical region model (or 3D regional information) is processed in synchrony with the cutting paths. For example, as the cutting path is about to enter a critical region at the device operating end-effector, the system generates an alert. As described in more detail below, the alert can display on the monitor with or without audio output to warn the surgeon that the device operating end-effector will be in proximity to anatomical structures inside the critical region. In some embodiments, when the critical region is entered, the device will halt cutting.

Determining a Correlation Between a Cut Region and Critical Regions: Generating an Alert As shown in FIG. 4, a specific inventive embodiment for monitoring a surgical procedure with critical regions may include decision block 440, which recites determining a correlation between a cut region and the critical regions.

Block 440 in certain embodiments functions to determine if the robot is within a defined proximity of a critical region.

A correlation between a cut region and the identified critical regions can be performed using any suitable process. In some embodiments, a correlation is determined to exist if the cut region is within a defined proximity to a critical region. The defined proximity can be, for example, a selected distance (or pixels) or include a partial or complete overlap.

For example, in some embodiments, a correlation is determined to exist if the instant cut region being evaluated overlaps at least partially with an identified critical region. In some embodiments, a correlation is determined to exist if a subsequent (or next) cut region overlaps at least partially with an identified critical region. In some embodiments, a correlation is determined to exist if any cut region in the cutting path overlaps at least partially with an identified critical region.

In another example, a correlation is determined to exist if the current cut region being evaluated is within a defined distance of an identified critical region. It will be appreciated that the distance between regions is expressed as a function of processing time and/or cutting speed (i.e., feed rate). Thus, the correlation may alternatively be based on time.

As described above, if it is determined that no correlation exists, the process moves to block 445 where an output robot motion command is generated for the cut region. The method returns to block 420 to process the next cut region in the cutting path. This iterative process can continue until a stop command is received, for example at block 465, block 475, or an emergency stop command.

Generating an Alert

As discussed above, when the process 400 determines that a selected correlation exists, an alert command can be generated as in block 450 of FIG. 4. Block 450 in some embodiments functions to gain the attention of the user.

Accordingly, the methods described herein can function to provide a warning to a user (for example, a surgeon) in a computer-controlled surgical procedure when the surgical device enters critical regions of the patient's body where critical tissue, vascular, or nerve damage can potentially take place.

The alert generated by the methods described herein additionally function to retain the user's attention throughout the computer-controlled surgical procedure, for example due to distraction or fatigue.

When the alert is presented to the surgeon, the surgeon is preferably required to acknowledge and thus allow the device to proceed cutting. This acknowledgement is received as a vigilance control button on a pendant that is held by the surgeon or a foot pedal that is activated by the surgeon. If the acknowledgement is not received, the device will not continue cutting, minimizing the hazard of undesirable cutting that could cause patient harm. However, if the warning is acknowledged before a critical region is entered, there is no interruption to the cutting, for example, during a non-critical-to-critical region transition or a critical-to-critical region transition.

Output Robot Motion Command

As shown in FIG. 4, in certain inventive embodiments for monitoring a surgical procedure with critical regions may include block 445, which recites generating an output robot motion command.

One approach to generating and implementing output robot motion commands is described in commonly owned U.S. Pat. No. 5,806,518. Additional approaches implementing output robot motion commands are described in the commonly owned U.S. patents and references disclosed and incorporated by reference herein. For example, the output robot motion commands may be used to control the robotic arm 28 and/or the effector 32.

Operator Controller

Also provided herein are methods of minimizing user fatigue during a semi-computer controlled surgical procedure. Generally, the method includes requiring a user generated acknowledgment in response to a computer generated alert as discussed in detail above. The user acknowledgment can be generated using a user controller that is minimally intrusive to the user experience. In some embodiments, a minimally intrusive controller requires a minimal amount of physical response from the user thereby being minimally intrusive to the user experience. A user controller may be selected for any number of desired features. One example of a suitable user controller is described in more detail below.

Figure 6:
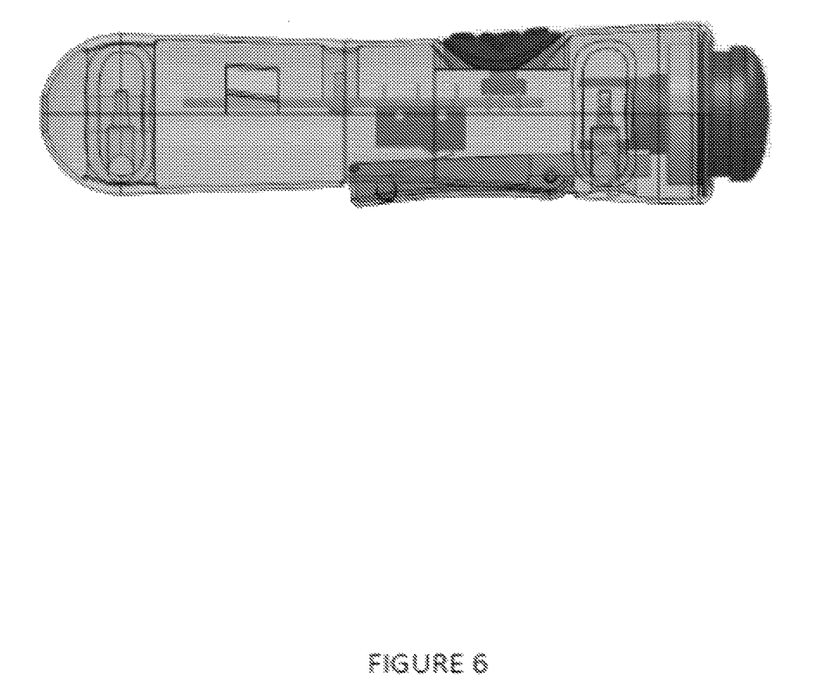
FIG. 6 illustrates an operator controller in accordance with some embodiments.

Existing user controllers require a user to physically contact the controller (for example by pushing a button) continuously throughout a procedure. This can result in fatigue and diverted attention in the user. A more ergonomic user controller that reduces surgeon fatigue is illustrated in FIG. 6.

In some embodiments, the user controller allows the user direct control of a surgical assistant device during the cutting operation. For example, the user controller can include two parts (1) an operator presence control (OPC) that allows the device's cutting procedure to continue, and (2) a monitor display that changes color to indicate the severity of a hazard. With the two combined, the indirect user's control is transformed to give the user more engaged supervisory control.

In some embodiments, because the preparation and setup of the surgical device does not contribute to the hazard to a patient, the user controller is only applicable during the cutting procedure. During cutting, the surgical device can automatically identify the distance of the cutting blades in relation to critical anatomical regions (as discussed above). The monitor in turn can display a background that changes from a cool color to a warm color as the distance decreases. In addition, the monitor can display a proximity meter to overcome difficulty of color blindness. In some embodiments, the cutting feed rate slows down to a halt if the OPC button is not pressed continuously. The cutter motor halts when the feed rate reaches zero. A halted cut can resume once the surgeon presses the OPC button.

The operator controller that combines an OPC and a color variable display engages the surgeon and mitigates the hazard of patient injury by a surgical device.

In the illustrated controller of FIG. 6, a control pendant with improved ergonomics and improved safety is provided. For example, the shape is smooth and rounded so it is comfortable to hold for long periods and comfortable to operate one handed. The linear "stack" of buttons on the existing pendant is replaced by a four-way navigation switch and a trigger. The navigation switch, operated with the thumb, includes a center-push for the "Menu" function in addition to left, right, up and down navigation. The "Select" function is attached to the trigger, which is operated with the first, second, and/or third finger(s) depending on the size of the user's hand. The emergency stop function is implemented with a dedicated, off-the-shelf switch designed for emergency stop use. It includes standard features such as a snap-in replaceable contact block and "push-to-stop, twist-to-reset" operation. The pendant body is intentionally designed around this standard emergency stop switch, making it accessible but not intrusive, by placing the e-stop at the front end of the assembly away from the other buttons.

Significant differences from typical video game controllers include the use of a hard-wired cable for all connections (wireless deemed too risky for hazard analysis), and a dedicated, latching Emergency Stop button which physically interrupts power to the robot motion controllers.

The illustrated pendant may use commercial-off-the-shelf (COTS) switch components integrated in user friendly packaging. For example, a COTS four-position navigation switch with center push is combined with a custom molded navigation button, providing the following functions: Up, Down, Left, Right, and Menu. In the design of accompanying software, these functions may be applied to navigation of the graphical user interface (GUI) and/or to direct control of robot motion (raising/lowering robot base, or fine adjustments to the position of any other axis of motion).

In some embodiments, a COTS snap-action roller-lever switch is combined with a custom molded trigger, torsion spring, and pivot pin to provide the following functions: Select, Operator Presence acknowledgment.

The trigger is intended to be operated throughout use of the robot to select or acknowledge menu items and respond to system messages (dialog boxes) or alerts generated by the system. The trigger may also be used to select valid digitizer points during bone registration. During cutting, the trigger may be used by the surgeon to approve each stage of the cutting process, based on feedback shown on the robot GUI display and on the state of the patient as discussed in detail above.

In some embodiments, the pendant body is designed as three separated injection molded shells, which assemble easily by hand using self-tapping screws. The top and bottom shells form the basic, curved shape of the pendant; the third shell holds the panel-mount emergency stop button in place and nests between top and bottom shells at the front end of the device. The emergency stop button's switch mechanism is prevented from rotating as it is held firmly between two screw mounting bosses with precise spacing.

The COTS switches can be attached to a printed circuit board which connects the individual switch elements to supply voltage, pull-up resistors, and individual wires in the pendant cable. The printed circuit board precisely locates the COTS switches relative to the top and bottom shells and to the molded navigation button and trigger, which are externally accessible to the user.

In some embodiments, the cable is led from the rear of the pendant, which will point back and down when held by the user. This should provide greater comfort compared to the "cable on top" design in the existing product. The cable is strain relieved and clamped between the top and bottom pendant shells, which include a molded-in cable clamp design. The cable is terminated inside the pendant body by a small, latching crimp housing connector (such as a Molex Picoblade or Harwin Datamate), removing the need to solder cables and pendants together in manufacturing.

It will be appreciated that the user acknowledgement commands (e.g., continue, pause, stop) can be generated using the buttons of the user controller described above.

Additional Features

In some embodiments, the system includes a system controller as described in commonly owned U.S. Pat. No. 5,806,518. The system controller positions the effector by moving the manipulatable arm.

In some embodiments, the end effector 32 is a rotary cutter, such as a disk cutter or a ball cutter as described in commonly owned U.S. Pat. No. 5,776,136.

In some embodiments, the system includes a six degree of freedom position sensor as described in commonly owned U.S. Pat. No. 6,332,567.

In some embodiments, the system includes a bone fixator as described in commonly owned U.S. Pat. No. 5,806,518.

In some embodiments, the system includes a bone digitizer arm as described in commonly owned U.S. Pat. Nos. 6,332,567 and 6,033,415.

In some embodiments, the system includes a plurality of position sensors for generating a digitized bone data set as described in commonly owned U.S. Pat. No. 6,033,415.

In some embodiments, the system includes a non-contact digitizing apparatus to generate a digitized bone data set as described in commonly owned U.S. Pat. No. 6,033,415.

In some embodiments, the system includes an angle indicator attached to the arm as described in commonly owned U.S. Patent Publication No. 2011/0152871.

In some embodiments, the system includes an impactor physically connected to an angle indicator with at least one flexible guide as described in commonly owned U.S. Patent Publication No. 2011/0152871.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for monitoring an operative site during a surgical procedure using a computer controlled surgical device, the method comprising:
   processing a defined cutting path having a cut region in a computer of the computer controlled surgical device;
   determining a correlation between the cut region and one or more critical regions to generate an alert indicative of a movable end-effector being within a defined proximity of the one or more critical regions;
   compromising a subject tissue in the cut region with the computer controlled surgical device and exclusive of the one or more critical regions; and
   requiring a user acknowledgment of the alert to allow processing of the cutting path to continue.

2. The method of claim 1, wherein the critical regions are determined based on at least one of: (a) known anatomical areas where arteries, veins, nerve bundles, cartilage, bone of a specific density or type, and tendons are located and (b) image-based processing that indicates arteries, veins, nerve bundles, cartilage, bone of a specific density or type, and tendons.

3. The method of claim 1, wherein the user acknowledgement is a command that includes at least one of (a) continue, (b) skip region, and (c) pause.

4. The method of claim 1, wherein the user acknowledgement is a command of continue and receipt of the continue command before an effector of the computer controlled surgical device enters the one or more critical regions allows processing of the cutting path to continue into the one or more critical regions without interruption.

5. The method of claim 1, wherein processing the cutting path is interrupted if the user acknowledgement is not received.

6. The method of claim 1, further comprising:
generating a cut file including cutting paths; and
storing the cut file in a tangible medium.

7. The method of claim 1, further comprising at least one of:
generating a 3-D model of the operative structure; and
generating a 3-D critical regions model with the critical regions.

8. The method of claim 7, wherein the 3-D model of the operative structure and the 3-D critical regions model are generated from a same source of image data.

9. The method of claim 7, wherein the critical regions are determined before processing the defined cutting path.

10. The method of claim 7, wherein the cutting path is processed in parallel with determining the critical regions.

11. The method of claim 7, wherein one or more critical regions is identified after the processing of the cutting path has begun.

12. The method of claim 7, wherein generating the 3-D critical regions model includes: performing a 3D analysis using a computer controlled device to distinguish critical regions from non-critical regions.

13. The method of claim 12, wherein the 3D analysis is performed with a semi-automatic segmentation of imaging data.

14. The method of claim 12, wherein the 3D analysis is performed by a manual method without artificial intelligence.

15. The method of claim 1, wherein the one or more critical regions are stored in a tangible medium as 3D volumes or points in space.

16. The method of claim 1, wherein the one or more critical regions are selected manually and intraoperatively by the user.

17. The method of claim 1, wherein the alert includes at least one of a visual or audio output.

18. The method of claim 1, wherein the acknowledgement is received as a vigilance control button on a surgeon input device, such as a pendant or foot pedal.

19. The method of claim 1, wherein the compromising of the subject tissue includes at least one of an incision, cutting, milling, drilling, puncturing, or piercing.

20. The method of claim 1, wherein the cut region is obscured from a user view.

21. The method of claim 1, wherein the correlation and alert is based on arm movement speed, feed rate, and time.

22. The method of claim 1, wherein the user acknowledgment is generated using a user controller.

23. The method of claim 22, wherein the user controller requires a physical response by the user only in the one or more critical regions.

* * * * *